United States Patent
Tate et al.

(10) Patent No.: US 11,456,164 B2
(45) Date of Patent: *Sep. 27, 2022

(54) SYSTEMS AND METHODS FOR IDENTIFYING COMPOUNDS FROM MS/MS DATA WITHOUT PRECURSOR ION INFORMATION

(71) Applicant: DH TECHNOLOGIES DEVELOPMENT PTE. LTD., Singapore (SG)

(72) Inventors: Stephen A. Tate, Barrie (CA); Ronald F. Bonner, New Market (CA)

(73) Assignee: DH Technologies Development Pte. Ltd., Singapore (SG)

(*) Notice: Subject to any disclaimer, the term of this patent is extended or adjusted under 35 U.S.C. 154(b) by 702 days.

This patent is subject to a terminal disclaimer.

(21) Appl. No.: 16/199,966

(22) Filed: Nov. 26, 2018

(65) Prior Publication Data

US 2019/0096647 A1 Mar. 28, 2019

Related U.S. Application Data

(63) Continuation of application No. 14/427,564, filed as application No. PCT/IB2013/002304 on Oct. 16, 2013, now Pat. No. 10,141,169.

(60) Provisional application No. 61/726,617, filed on Nov. 15, 2012.

(51) Int. Cl.
| | |
|---|---|
| *G01N 33/48* | (2006.01) |
| *G01N 33/50* | (2006.01) |
| *H01J 49/00* | (2006.01) |
| *G16C 20/20* | (2019.01) |
| *G16C 99/00* | (2019.01) |

(52) U.S. Cl.
CPC .......... *H01J 49/0036* (2013.01); *G16C 20/20* (2019.02); *G16C 99/00* (2019.02); *H01J 49/004* (2013.01)

(58) Field of Classification Search
CPC .... H01J 49/0036; H01J 49/004; G16C 99/00; G16C 20/20
See application file for complete search history.

(56) References Cited

U.S. PATENT DOCUMENTS

| | | | | |
|---|---|---|---|---|
| 5,538,897 A | * | 7/1996 | Yates, III | C07K 1/00 436/89 |
| 10,141,169 B2 | * | 11/2018 | Tate | H01J 49/0036 |
| 2007/0136007 A1 | * | 6/2007 | Bern | G16B 50/00 702/27 |

FOREIGN PATENT DOCUMENTS

WO   WO-2006040622 A1 * 4/2006 ............. G16C 20/20

OTHER PUBLICATIONS

Gillet et al. Targeted data extraction of the MS/MS spectra generated by data-independent acquisition: a new concept for consistent and accurate proteome analysis. Molecular & Cellular Proteomics 11.6, Jan. 18, 2012, 17 pages.*
Wolf et al. In silico fragmentation of computer assisted identification of metabolite mass spectra. BMC Bioinformatics, vol. 11, article 148, 12 pages. (Year: 2010).*

* cited by examiner

*Primary Examiner* — Russell S Negin
(74) *Attorney, Agent, or Firm* — Kasha Law LLC; John R. Kasha; Kelly L. Kasha (57) ABSTRACT

Systems and methods are provided for identifying a precursor ion without using any a priori precursor ion information. In one method, a sample is analyzed using a tandem mass spectrometer, producing at least one measured product ion spectrum from a precursor mass-to-charge ratio range. The at least one measured product ion spectrum are received. A subset of measured product ions is selected from the at least one measured product ion spectrum. A list of candidate compounds is created by searching a dictionary of potential compounds that includes one or more predicted product ions for each of the potential compounds using the subset of measured product ions. A candidate compound on the list is selected as the identified compound. In another method, the measured product ions are assumed to correspond to shortened forms of the peptide and a protein database is searched for shortened forms of the peptide.

20 Claims, 5 Drawing Sheets

Specification includes a Sequence Listing.

SEQUENCE LISTING

<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Example

<400> SEQUENCE: 1

Lys Ala Cys Asp Glu Phe Gly His Arg
1               5

<210> SEQ ID NO 2
<211> LENGTH: 8
<212> TYPE: PRT
<213> ORGANISM: Artificial Sequence
<220> FEATURE:
<223> OTHER INFORMATION: Example

<400> SEQUENCE: 2

Ala Cys Asp Glu Phe Gly His Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Example

<400> SEQUENCE: 3

Ala Cys Asp Glu Phe Gly His
1               5

<210> SEQ ID NO 4
<211> LENGTH: 6
<212> TYPE: PRT
<213> ORGANISM: Artificial Sequence
<220> FEATURE:
<223> OTHER INFORMATION: Example

<400> SEQUENCE: 4

Ala Cys Asp Glu Phe Gly
1               5

```
<210> SEQ ID NO 5
<211> LENGTH: 5
<212> TYPE: PRT
<213> ORGANISM: Artificial Sequence
<220> FEATURE:
<223> OTHER INFORMATION: Example

<400> SEQUENCE: 5

Ala Cys Asp Glu Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Example

<400> SEQUENCE: 6

Cys Asp Glu Phe Gly His Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Example

<400> SEQUENCE: 7

Asp Glu Phe Gly His Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Example

<400> SEQUENCE: 8

Glu Phe Gly His Arg
1               5
```

SYSTEMS AND METHODS FOR IDENTIFYING COMPOUNDS FROM MS/MS DATA WITHOUT PRECURSOR ION INFORMATION

CROSS REFERENCE TO RELATED APPLICATION

This application is a continuation of U.S. patent application Ser. No. 14/427,564, filed Mar. 11, 2015, filed as Application No. PCT/IB2013/002304 on Oct. 16, 2013, which claims the benefit of U.S. Provisional Patent Application Ser. No. 61/726,617, filed Nov. 15, 2012, the content of which is incorporated by reference herein in its entirety.

INTRODUCTION

In general, the identification of compounds by tandem mass spectrometry, or mass spectrometry/mass spectrometry (MSMS), requires the mass of a known or experimentally derived precursor ion (which is the molecular weight if the charge state is known). Selected reaction monitoring (SRM) is a well-known example of a method that requires the mass of a known precursor ion. For example, in an SRM method a precursor ion is selected, fragmented, and passed to a second analyzer which is set to transmit a single ion. A response is generated when a precursor of the selected mass fragments to give an ion of the selected fragment mass, and this output signal can be used for quantitation. The instrument may also be set to measure several fragment ions for identification purposes or several precursor-fragment combinations to quantitate different compounds.

In some methods of tandem mass spectrometry, however, the mass of the precursor ion may not be known. For example, in a tandem mass spectrometry technique called sequential windowed acquisition (SWATH), the mass of the precursor ion may not be known. SWATH allows a mass range to be scanned within a time interval using multiple scans with adjacent or overlapping precursor mass windows. A first mass analyzer selects each precursor mass window for fragmentation. A high resolution second mass analyzer is then used to detect the product ions produced from the fragmentation of each precursor mass window. Identification of the correct precursor ion for a set of product ions can, therefore, be confounded by the presence of many other precursor ions within a precursor mass window.

In addition, the mass of a known or experimentally derived precursor ion may not identify the compound of interest. For example, if the compound of interest is a peptide and the compound analyzed is a modified peptide, the precursor ion selected for fragmentation may not indicate the molecular weight of the unmodified (naked) peptide.

SUMMARY

A system is disclosed for identifying a compound from tandem mass spectrometry product ions without using any a priori precursor ion information. In various embodiments, the system includes a tandem mass spectrometer that analyzes a sample producing at least one measured product ion spectrum from a precursor mass-to-charge ratio range. The system also includes a processor that receives the at least one measured product ion spectrum from the tandem mass spectrometer. The processor selects a subset of measured product ions from the at least one measured product ion spectrum. The processor creates a list of candidate compounds that includes a score for each of the candidate compounds. The processor creates the list by searching a dictionary of potential compounds using the subset of measured product ions. The processor selects a candidate compound from the list as the identified compound.

A method is disclosed for identifying a compound from tandem mass spectrometry product ions without using any a priori precursor ion information. In various embodiments, a sample is analyzed using a tandem mass spectrometer, producing at least one measured product ion spectrum from a precursor mass-to-charge ratio range. The at least one measured product ion spectrum are received from the tandem mass spectrometer using a processor. A subset of measured product ions is selected from the at least one measured product ion spectrum using the processor. A list of candidate compounds is created that includes a score for each of the candidate compounds by searching a dictionary of potential compounds that includes one or more predicted product ions for each of the potential compounds using the subset of measured product ions using the processor. Finally, a candidate compound on the list is selected as the identified compound using the processor.

A computer program product is disclosed that includes a non-transitory and tangible computer-readable storage medium whose contents include a program with instructions being executed on a processor so as to perform a method for identifying a compound from tandem mass spectrometry product ions without using any a priori precursor ion information. In various embodiments, the method includes providing a system, wherein the system comprises one or more distinct software modules, and wherein the distinct software modules comprise a measurement module and an identification module. In various embodiments, the measurement module receives from a tandem mass spectrometer at least one measured product ion spectrum from a precursor mass-to-charge ratio range produced by analyzing a sample. The identification module selects a subset of measured product ions from the at least one measured product ion spectrum. The identification module creates a list of candidate compounds that includes a score for each of the candidate compounds. The identification module creates the list by searching a dictionary of potential compounds that includes one or more predicted product ions for each of the potential compounds using the subset of measured product ions. The identification module selects a candidate compound from the list as the identified compound.

A system is also disclosed for identifying a peptide from tandem mass spectrometry product ions assumed to correspond to shortened forms of the peptide without using any a priori precursor ion information. In various embodiments, the system includes a tandem mass spectrometer that analyzes a sample producing at least one measured product ion spectrum from a precursor mass-to-charge ratio range. The system also includes a processor that receives the at least one measured product ion spectrum from the tandem mass spectrometer. In addition, the processor further selects the subset of measured product ions from the at least one measured product ion spectrum by selecting a number of measured mono-isotopic product ions from the at least one measured product ion spectrum with the highest intensity and with an m/z greater than the precursor m/z range. The processor then searches a protein database in a non-tryptic or semi-tryptic mode specifying the subset of measured product ions as the precursor ions for the search. Finally, the processor selects a full length tryptic peptide from the search results that has a mass to charge ratio in the precursor mass-to-charge ratio range and a non-tryptic or semi-tryptic form with a mass-to-charge ratio matching one of the subset of measured product ions as the identified peptide.

A method is also disclosed for identifying a peptide from tandem mass spectrometry product ions assumed to correspond to shortened forms of the peptide without using any a priori precursor ion information. In various embodiments, a sample is analyzed using a tandem mass spectrometer, producing at least one measured product ion spectrum from a precursor mass-to-charge ratio range. The at least one measured product ion spectrum are received from the tandem mass spectrometer using a processor. A subset of measured product ions is selected from the at least one measured product ion spectrum by selecting a number of measured mono-isotopic product ions from the at least one measured product ion spectrum with the highest intensity and with a mass-to-charge ratio greater than the precursor mass-to-charge ratio range using the processor. A protein database is searched in a non-tryptic or semi-tryptic mode specifying the subset of measured product ions as the precursor ions for the search using the processor. Finally, a full length tryptic peptide is selected from the search results that has a mass to charge ratio in the precursor mass-to-charge ratio range and a non-tryptic or semi-tryptic form with a mass-to-charge ratio matching one of the subset of measured product ions as the identified peptide using the processor.

A computer program product is also disclosed that includes a non-transitory and tangible computer-readable storage medium whose contents include a program with instructions being executed on a processor so as to perform a method for identifying a peptide from tandem mass spectrometry product ions assumed to correspond to shortened forms of the peptide without using any a priori precursor ion information. In various embodiments, the method includes providing a system, wherein the system comprises one or more distinct software modules, and wherein the distinct software modules comprise a measurement module and an identification module. The measurement module receives from a tandem mass spectrometer at least one measured product ion spectrum from a precursor mass-to-charge ratio range produced by analyzing a sample. The identification module selects a subset of measured product ions from the at least one measured product ion spectrum by selecting a number of measured mono-isotopic product ions from the at least one measured product ion spectrum with the highest intensity and with a mass-to-charge ratio greater than the precursor mass-to-charge ratio range. The identification module searches a protein database in a non-tryptic or semi-tryptic mode specifying the subset of measured product ions as the precursor ions for the search. The identification module selects a full length tryptic peptide from the search results that has a mass to charge ratio in the precursor mass-to-charge ratio range and a non-tryptic or semi-tryptic form with a mass-to-charge ratio matching one of the subset of measured product ions as the identified peptide.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
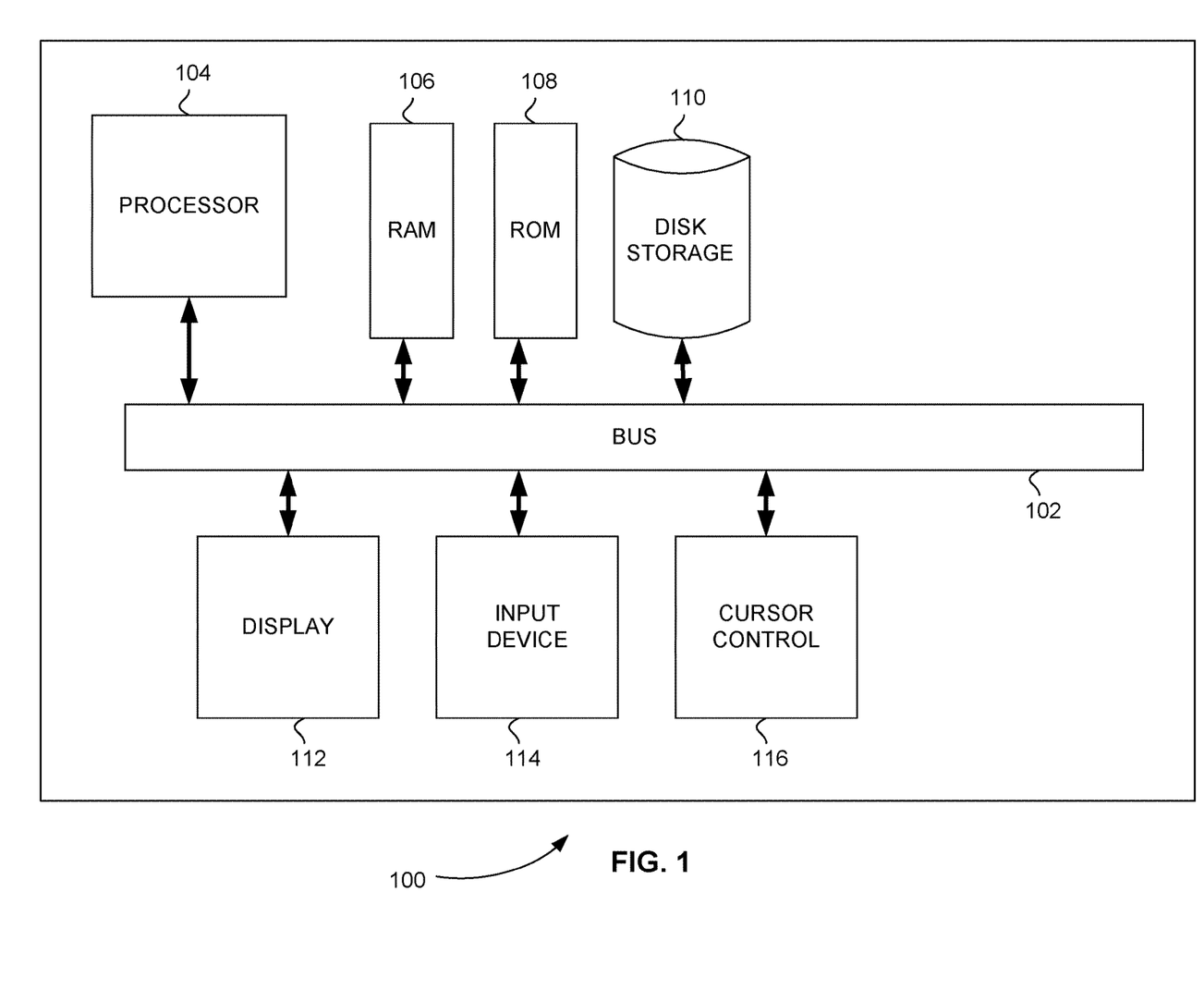
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Identifying Compounds

As described above, the identification of compounds by tandem mass spectrometry, or mass spectrometry/mass spectrometry (MS/MS), generally requires the mass of a known or experimentally derived precursor ion. In some methods of tandem mass spectrometry, such as sequential windowed acquisition (SWATH), however, the mass of the precursor ion may not be known. In addition, the mass of a known or experimentally derived precursor ion may not identify the compound of interest due to a modification of the compound of interest in the sample analyzed.

In various embodiments, the identity of a compound is determined without knowing the mass of a known or experimentally derived precursor ion. In one embodiment, identification can be determined based on the uniqueness of one or more product ions. In another embodiment, a database search can be conducted by assuming that a product ion is a shortened form of a precursor ion.

In both embodiments, the identity of product ions is assumed to help identify the peptide. In the first embodiment, it is assumed that the ions are actual product ions from a precursor ion of unknown (but restricted) m/z. In the second embodiment, it is assumed that the ions are precursor ions (of a shortened fragment).

Search Based on Product Ions

Although the following discussion involves proteins and peptides, the systems and methods described herein can be used for other compounds, if the fragments of these compounds can be predicted. Given a list of likely proteins in a sample, for example, the peptides of the proteins and then the fragment ions of the peptides can be predicted.

In various embodiments, a dictionary is created for all possible fragment or product ion masses of likely peptides in a proteome. Here a dictionary is a computer data structure that uses keys to store data in an organized way. Values are stored with specific keys so that the key can be used to retrieve only those values. In this case, the key is the calculated mass of the product ion and the value is a list of all peptides (sequences or other identifiers) that could produce the mass of the product ion. For each product ion mass, a list of the corresponding peptides and/or proteins is stored in the dictionary. The dictionary can be stored in a database, for example. The sample is then analyzed using a tandem mass spectrometer, producing a product ion spectrum.

In one embodiment, a peptide is identified by:
A. Selecting a product ion from the product ion spectrum and retrieving the list of possible peptides that could generate that product ion from the dictionary.
B. Selecting another product ion from the product ion spectrum and retrieving another list of possible peptides that could generate that product ion from the dictionary.
C. Examining the lists retrieved and identifying peptides common to all the lists retrieved.
D. Repeating steps B-C until just one peptide is identified from the lists retrieved.

In another embodiment, a peptide is identified by:
A. Selecting a product ion from the product ion spectrum and retrieving a list of possible peptides that could generate that product ion from the dictionary.
B. For each peptide on the list, predicting the other product ions that the peptide would produce by searching the database of peptides.
C. For each peptide on the list, comparing the predicted product ions with the product ion spectrum to determine the best matching peptide.

In various embodiments, the ions corresponding to the identified peptide can be removed from the product ion spectrum and the identification procedure repeated to identify additional peptides that may have been selected and fragmented.

In various embodiments, the performance of both of these methods can be improved by selecting the most specific product ions first. The most specific product ions are, for example, those that appear in the smallest number of peptides. Starting with the smallest number of peptides makes subsequent processing faster.

This information is already in the dictionary of product ion masses and peptides as the most specific masses will have the shortest lists of peptides that could generate those masses. As a result, in various embodiments, step A in both of the methods described above can be replaced with:

A. Selecting a product ion from the product ion spectrum that has the fewest number of peptides and retrieving a list of possible peptides that could generate that product ion.

Search Based on a Product Ion Assumed to be a Precursor Ion

In various embodiments, it is also possible to perform searches using a derived product ion spectrum and using a mass within the product ion spectrum as the precursor ion. This approach relies on the observation that ions above the precursor ion are likely to be y ions, which correspond chemically to the molecular ion that would be observed from a shortened version of the peptide (missing N-terminal residues). Thus, if non-tryptic or semi-tryptic peptides are allowed in the search, these spectra will be returned as non-tryptic or semi-tryptic forms of the correct peptide.

Database search engines that are typically used to identify peptides normally assume that a peptide is "fully tryptic." In other words, these search engines assume that the peptide is generated by cleavage on the C-terminal side of the amino acids K and R:

(protein N-Terminus)—xxxK.ACDEFGHR.xxxxx—(protein C-terminus)

where the dots represent the enzyme cleavage sites and the final, fully tryptic peptide is ACDEFGHR.

However, most search engines allow the use of "semi-tryptic" peptides, where one of the peptide ends does not correspond to a tryptic site, i.e., in the above example they are ACDEFGH, ACDEFG, ACDEF, etc. (non-tryptic C-terminal cleavage) or CDEFGHR, DEFGHR, EFGHR, etc. (non-tryptic N-terminal cleavage site). The latter forms correspond to y ions generated by fragmenting the intact peptide.

In various embodiments, therefore, the peptide can be identified using a conventional search engine if the mass of a y ion is used as if it were the precursor ion and the semi-tryptic mode of operation is identified.

In fact, fragmenting a multiply charged precursor ion can generate ions with a higher mass-charge value (m/z, as measured by a mass spectrometer) if z is reduced, and these ions often correspond to y ions.

In various embodiments, a method for identifying a peptide proceeds as follows:

A. Given the product ion spectrum of a multiply charged ion, select the highest mono-isotopic ion in the spectrum—$m_{max}$ B. Send the product ion spectrum to a search engine passing $m_{max}$ as the precursor ion mass and select the semi-tryptic mode.

This method is performed for 2 or 3 m/z values, since it is possible that the ions are not y ions. If the ions are all y ions, then different length shortened forms of the fully tryptic peptide will be received.

Compound Identifying Systems

Another conventional method of identifying a protein in a sample using tandem mass spectrometry involves comparing an entire measured product ion spectrum to a database of predicted product ion spectra. Sub-sequences (or peptides) for known or target proteins are determined from a sequence library and predicted product ion spectra are created from the peptides using a computer. An unknown peptide is then identified using tandem mass spectrometry by comparing an entire measured product ion spectrum to the predicted product ion spectra. An entire measured product ion spectrum is compared to a predicted product ion using a closeness-of-fit algorithm, for example.

Typically in such a conventional method of identifying a protein in a sample some a priori knowledge about the unknown peptide is used. For example, the known mass of the unknown peptide is used to generate the predicted product ion spectra.

As described above, however, in many cases no a priori knowledge about the unknown peptide is available. As a result, in various embodiments systems and methods are disclosed for identifying an unknown precursor ion from tandem mass spectrometry data without using any a priori precursor ion information.

System for Search Based on Product Ions

In various embodiments, instead of predicting an entire product ion spectrum and comparing it to a measured product ion spectrum, one product ion is predicted and compared to the measured product ion spectrum at a time. An unknown peptide or precursor ion is then identified based the number of predicted product ions that matched the measured product ion spectrum.

Figure 2:
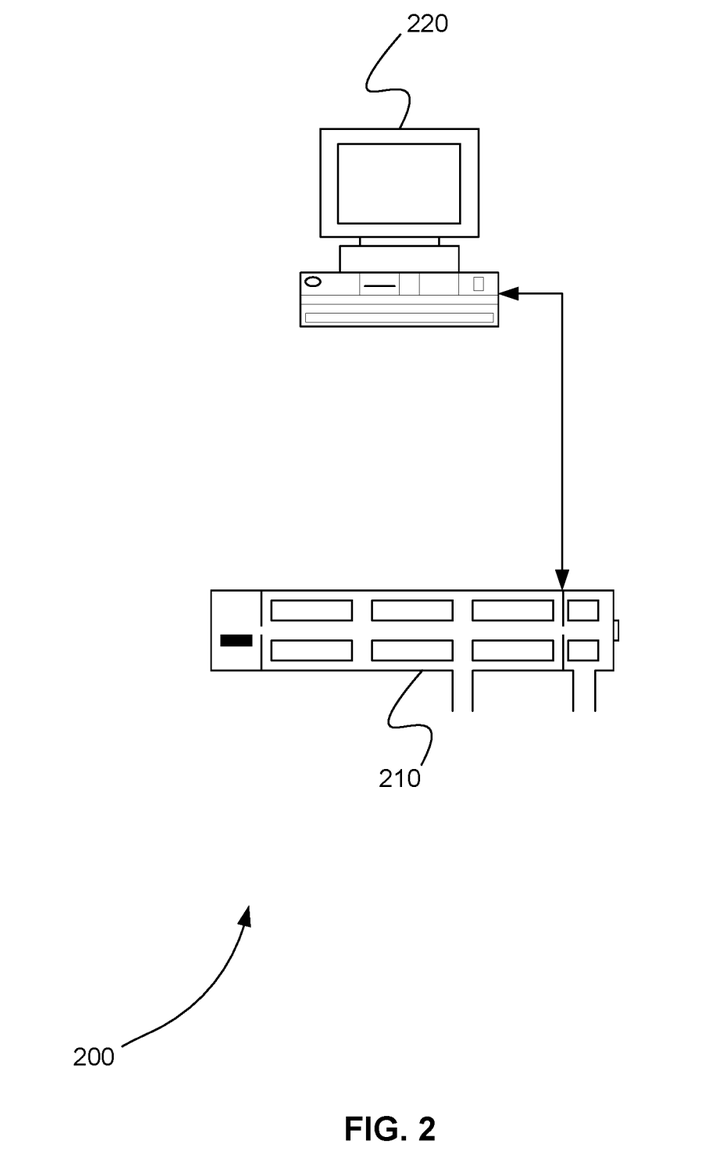
FIG. 2 is a schematic diagram showing a system for identifying a compound from tandem mass spectrometry product ions without using any a priori precursor ion information, in accordance with various embodiments.

FIG. 2 is a schematic diagram showing a system 200 for identifying a compound from tandem mass spectrometry product ions without using any a priori precursor ion information, in accordance with various embodiments. System 200 includes tandem mass spectrometer 210 and processor 220.

Tandem mass spectrometer 210 can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, or a Fourier transform mass analyzer. Tandem mass spectrometer 210 can also include a separation device (not shown). The separation device can perform a separation technique that includes, but is not limited to, liquid chromatography, gas chromatography, capillary electrophoresis, or ion mobility. Tandem mass spectrometer 210 can include separating mass spectrometry stages or steps in space or time, respectively.

Processor 220 can be, but is not limited to, a computer, microprocessor, or any device capable of sending and receiving control signals and data from tandem mass spectrometer 210 and processing data. Processor 220 is in communication with tandem mass spectrometer 210.

In one embodiment of system 200, tandem mass spectrometer 210 analyzes a sample producing at least one measured product ion spectrum from a precursor mass-to-charge ratio range. A precursor mass-to-charge ratio range is, for example, a precursor mass window. In various embodiments, tandem mass spectrometer 210 analyzes the sample using SWATH. Tandem mass spectrometer 210 divides a mass range into two or more precursor mass windows, for example. Tandem mass spectrometer 210 then fragments each precursor mass window of the two or more mass windows, producing a measured product ion spectrum for each precursor mass window.

Processor 220 receives the at least one measured product ion spectrum from tandem mass spectrometer 210. Processor 220 selects a subset of measured product ions from the at least one measured product ion spectrum. The subset includes a number of product ions large enough to identify an unknown precursor ion from other ions, for example. An exemplary number of product ions selected for the subset is 30.

Processor 220 creates a list of candidate compounds that includes a score for each of the candidate compounds. For example, a score can be a count of the number of times a candidate compound matches a measured product ion of the subset of measured product ions. Processor 220 creates the list by searching a dictionary of potential compounds using the subset of measured product ions. The dictionary includes one or more predicted product ions for each of the potential compounds. Processor 220 selects a candidate compound from the list as the identified compound. For example, the candidate compound with the highest score is selected as the identified compound.

In various embodiments, the sample includes proteins or peptides and the identified compound is a peptide. For example, the measured product ion spectrum includes peptide fragments, the dictionary of potential compounds includes predicted peptides for proteins, the one or more predicted product ions for each of the potential compounds include one or more fragments of peptides, and the list of candidate compounds includes candidate peptides.

In various embodiments, the sample includes compounds other than proteins. For example, the sample includes sugars, lipids, deoxyribonucleic acid (DNA), ribonucleic acid (RNA), or any compound for which product ions can be predicted.

In various embodiments, filtering is performed on the measured product ion spectrum in order to select the subset of measured product ions. For example, processor 220 can select the subset of measured product ions by selecting a number of measured mono-isotopic product ions with the highest intensity from the at least one measured product ion spectrum. Alternatively or in combination with any preceding example, processor 220 can select the subset of measured product ions by selecting measured product ions predicted to occur in the smallest number of potential compounds. Alternatively or in combination with any preceding example, processor 220 can select the subset of measured product ions by selecting a number of measured product ions from the at least one measured product ion spectrum with a mass-to-charge ratio (m/z) greater than a threshold value.

In various embodiments, processor 220 creates the list of candidate compounds by searching the dictionary for potential compounds matching one measured product ion from the subset of measured product ions. The remainder of the measured product ions in the subset are then compared to the candidate compounds on the list to determine a candidate compound that has the most product ions in common with the subset of measured product ions.

For example, processor 220 selects a first product ion from a subset of measured product ions. Processor 220 searches the dictionary of potential compounds for potential compounds that include a predicted product ion that matches the first product ion, producing a plurality of matching potential compounds. Processor 220 adds the matching potential compounds to the list of candidate compounds and provides each candidate compound on the list with an initial score. For each remaining measured product ion from the subset of measured product ions, processor 220 iteratively compares each remaining product ion to the predicted product ions of each candidate compound on the list and increases the score of each candidate compound if an included predicted product ion matches a remaining measured product ion.

In various embodiments, processor 220 creates the list of candidate compounds by iteratively searching the dictionary with each measured product ion from the selected subset. If a candidate compound that matches the measured product ion is found, it is added to the candidate list if it is not already on the list. If a candidate compound that matches the measured product ion is already on the list, its score is increased.

For example, for each measured product ion from the subset of measured product ions, processor 220 searches the dictionary of potential compounds for potential compounds that include a predicted product ion that matches the measured product ion. If a potential compound includes a predicted product ion that matches the measured product ion, processor 220 adds the matching potential compound to the list of candidate compounds with an initial score, if the matching potential compound is not already on the list. Processor 220 increments the score of the matching potential compound, if the matching potential compound is already on the list.

In various embodiments, processor 220 further determines if the identified compound is a modified form. For example, processor 220 compares the identified compound to the precursor mass-to-charge ratio (m/z) range. If the identified compound m/z is not found in the precursor m/z range, processor 220 determines that the identified compound is a modified form.

In various embodiments, the unmodified form of the identified is found from the modified form. For example, processor 220 analyzes a list of modifications to determine a modification that puts the m/z of the modified identified compound in the precursor m/z range. The list of modifications is found from a database of modifications for compounds, for example.

In various embodiments, if the sample is a mixture, processor 220 further identifies one or more additional compound from the sample after a first compound is identified. For example, processor 220 further subtracts predicted product ions of the identified compound from the measured product ion spectrum. Processor 220 removes all candidate compounds currently on the list of candidate compounds. Processor 220 then selects a new subset of measured product ions from the measured product ion spectrum. Processor 220 creates a new list of candidate compounds that includes a score for each of the candidate compounds of measured product ions. Processor 220 creates the list by searching a dictionary of potential compounds using the subset of measured product ions. Processor 220 identifies a candidate compound on the list as the second identified compound.

System for Search Based on a Product Ion Assumed to Correspond to a Shortened Form of a Peptide In various embodiments, it is assumed that the compound to be identified is a peptide and a measured product ion is a modification of the peptide. The modification may be a truncation of the N-terminus to produce a shortened peptide with the same C-terminus, for example.

In another embodiment of system 200 in FIG. 2, tandem mass spectrometer 210 also analyzes a sample producing at least one measured product ion spectrum from a precursor mass-to-charge ratio range. In addition, processor 220 also receives the at least one measured product ion spectrum from tandem mass spectrometer 210 and selects a subset of measured product ions from the at least one measured product ion spectrum.

However, processor 220 further selects the subset of measured product ions from the at least one measured product ion spectrum by selecting a number of measured mono-isotopic product ions from the at least one measured product ion spectrum with the highest intensity and with an m/z greater than the precursor m/z range. Processor 220 then searches a protein database in a non-tryptic or semi-tryptic mode specifying the subset of measured product ions as the precursor ions for the search. Finally, processor 220 selects a full length tryptic peptide from the search results that has a mass to charge ratio in the precursor mass-to-charge ratio range and a non-tryptic or semi-tryptic form with a mass-to-charge ratio matching one of the subset of measured product ions as the identified peptide.

In various embodiments, if the sample is a mixture, processor 220 further identifies one or more additional compounds from the sample after a first compound is identified. For example, processor 220 subtracts predicted product ions of the identified peptide from the measured product ion spectrum. Processor 220 then selects a new subset of measured product ions from the at least one measured product ion spectrum by selecting a number of measured mono-isotopic product ions from the at least one measured product ion spectrum with the highest intensity and with an m/z greater than the precursor m/z range. Processor 220 then searches a protein database in a non-tryptic or semi-tryptic mode specifying the new subset of measured product ions as the precursor ions for the search. Finally, processor 220 selects a full length tryptic peptide from the search results that has a mass to charge ratio in the precursor mass-to-charge ratio range and a non-tryptic or semi-tryptic form with a mass-to-charge ratio matching one of the subset of measured product ions as the second identified peptide.

Compound Identifying Methods
Method for Search Based on Product Ions

Figure 3:
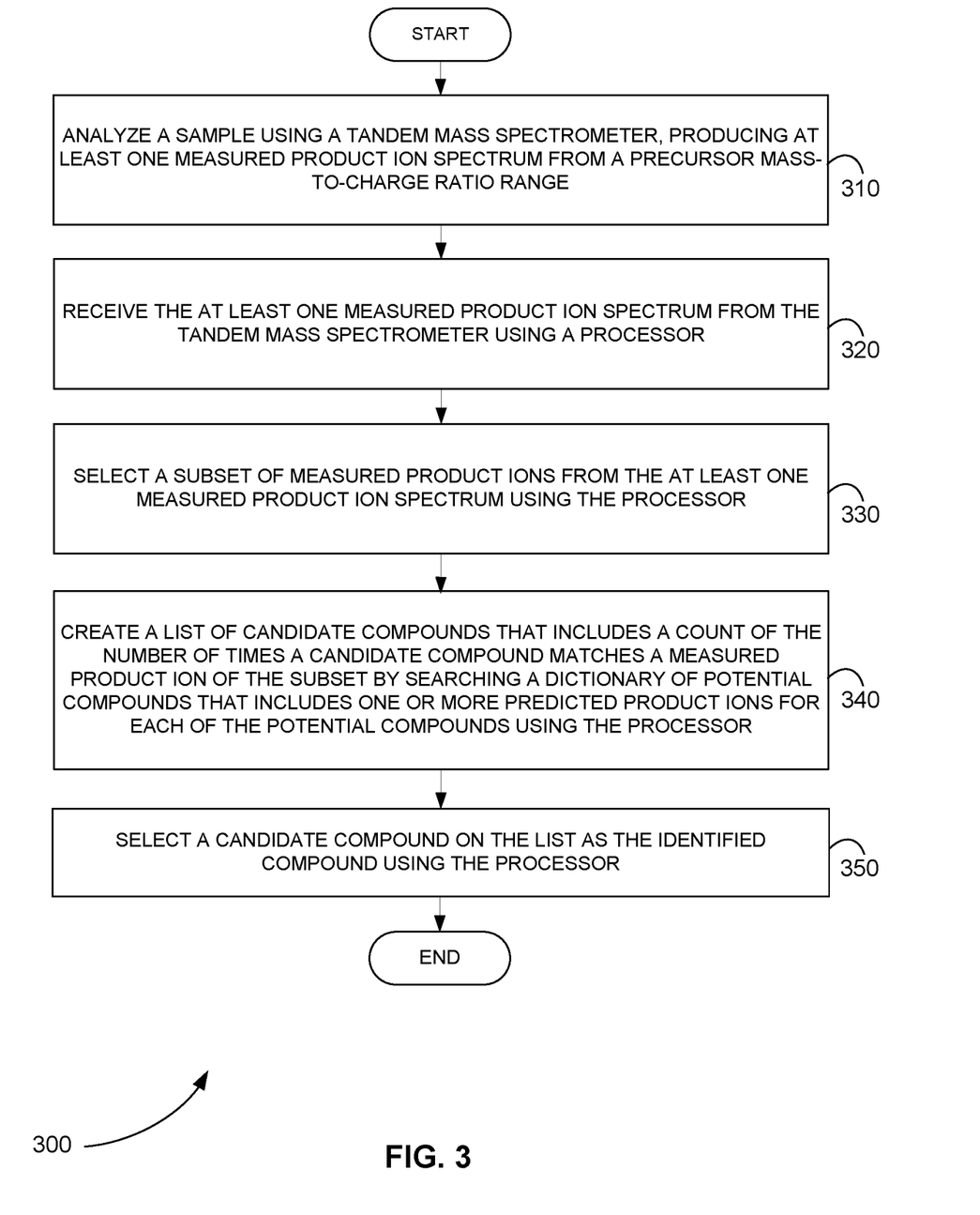
FIG. 3 is an exemplary flowchart showing a method for identifying a compound from tandem mass spectrometry product ions without using any a priori precursor ion information, in accordance with various embodiments.

FIG. 3 is an exemplary flowchart showing a method 300 for identifying a compound from tandem mass spectrometry product ions without using any a priori precursor ion information, in accordance with various embodiments.

In step 310 of method 300, a sample is analyzed using a tandem mass spectrometer, producing at least one measured product ion spectrum from a precursor mass-to-charge ratio range.

In step 320, the at least one measured product ion spectrum are received from the tandem mass spectrometer using a processor.

In step 330, a subset of measured product ions is selected from the at least one measured product ion spectrum using the processor.

In step 340, a list of candidate compounds is created that includes a score for each of the candidate compounds by searching a dictionary of potential compounds that includes one or more predicted product ions for each of the potential compounds using the subset of measured product ions using the processor.

In step 350, a candidate compound on the list is selected as the identified compound using the processor.

Figure 4:
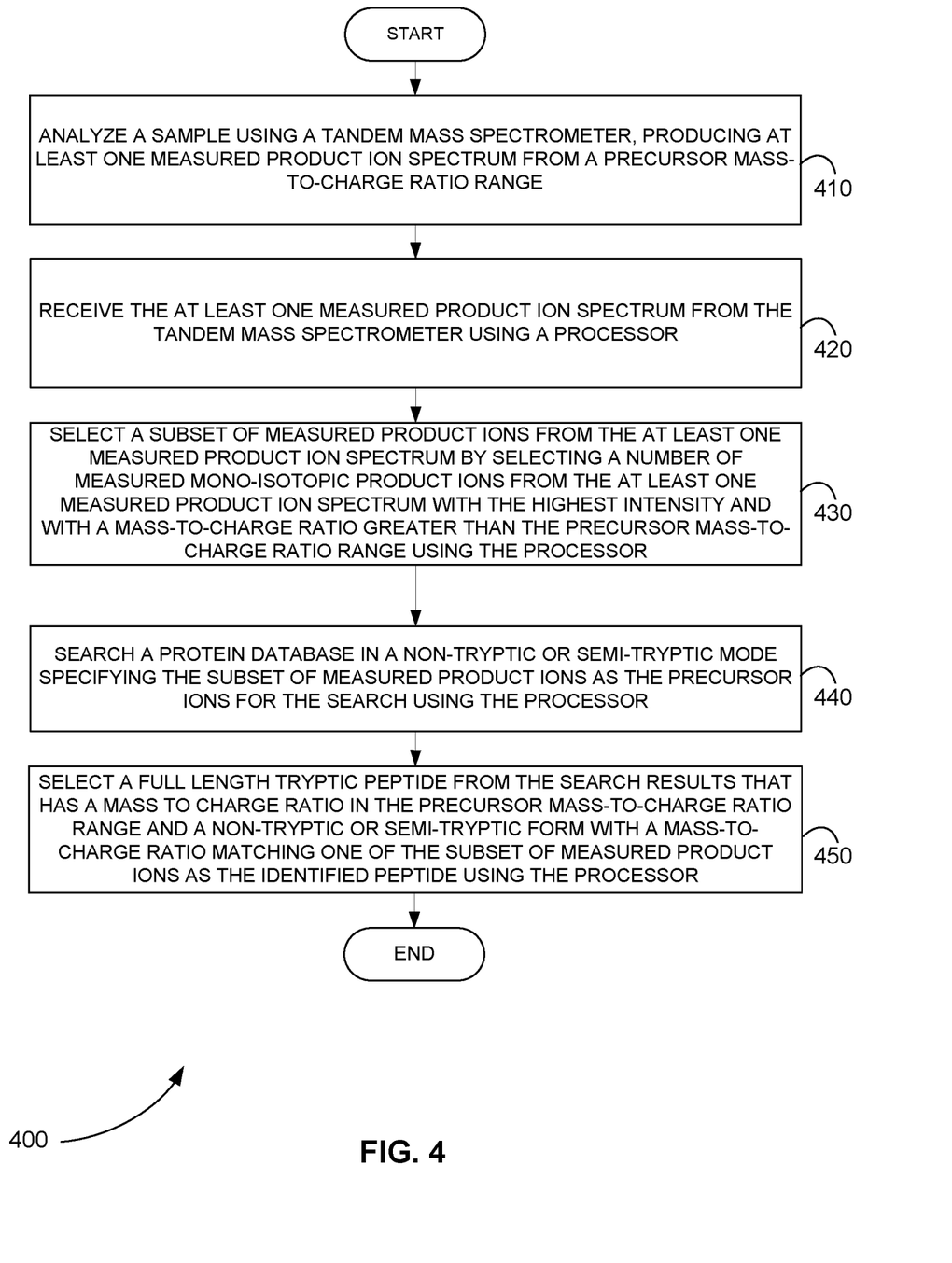
FIG. 4 is an exemplary flowchart showing a method for identifying a peptide from tandem mass spectrometry product ions assumed to correspond to shortened forms of the peptide without using any a priori precursor ion information, in accordance with various embodiments.

Method for Search Based on a Product Ion Assumed to Correspond to a Shortened Form of a Peptide FIG. 4 is an exemplary flowchart showing a method 400 for identifying a peptide from tandem mass spectrometry product ions assumed to correspond to shortened forms of the peptide without using any a priori precursor ion information, in accordance with various embodiments.

In step 410 of method 400, a sample is analyzed using a tandem mass spectrometer, producing at least one measured product ion spectrum from a precursor mass-to-charge ratio range.

In step 420, the at least one measured product ion spectrum are received from the tandem mass spectrometer using a processor.

In step 430, a subset of measured product ions is selected from the at least one measured product ion spectrum by selecting a number of measured mono-isotopic product ions from the at least one measured product ion spectrum with the highest intensity and with a mass-to-charge ratio greater than the precursor mass-to-charge ratio range using the processor.

In step 440, a protein database is searched in a non-tryptic or semi-tryptic mode specifying the subset of measured product ions as the precursor ions for the search using the processor.

In step 450, a full length tryptic peptide is selected from the search results that has a mass to charge ratio in the precursor mass-to-charge ratio range and a non-tryptic or semi-tryptic form with a mass-to-charge ratio matching one of the subset of measured product ions as the identified peptide using the processor.

Compound Identifying Computer Program Products
Computer Program Product for Search Based on Product Ions In various embodiments, computer program products include a tangible computer-readable storage medium whose contents include a program with instructions being executed on a processor so as to perform a method for identifying a compound from tandem mass spectrometry product ions without using any a priori precursor ion information. This method is performed by a system that includes one or more distinct software modules.

Figure 5:
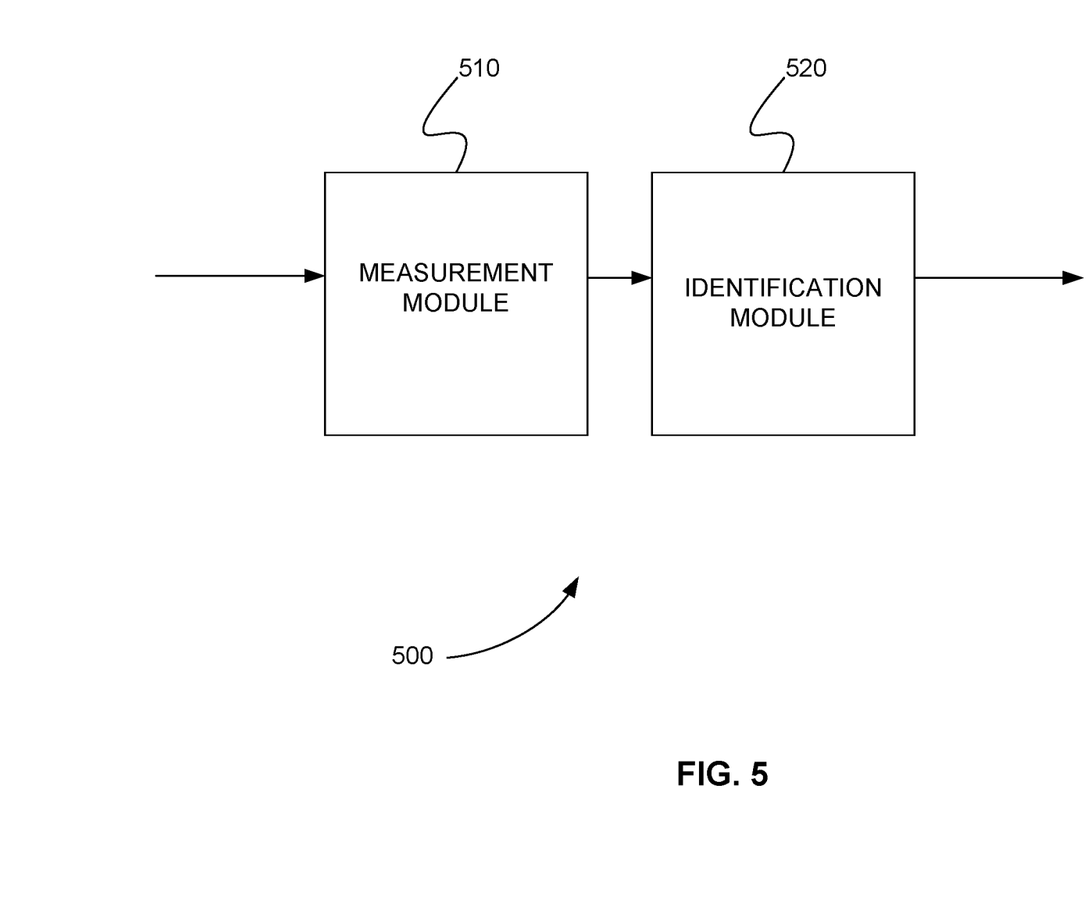
FIG. 5 is a schematic diagram of a system that includes one or more distinct software modules that performs a method for identifying a compound from tandem mass spectrometry product ions without using any a priori precursor ion information, in accordance with various embodiments.

FIG. 5 is a schematic diagram of a system 500 that includes one or more distinct software modules that performs a method for identifying a compound from tandem mass spectrometry product ions without using any a priori precursor ion information, in accordance with various embodiments. System 500 includes measurement module 510 and identification module 520.

Computer Program Product for Search Based on Product Ions

In one embodiment of system 500 shown in FIG. 5, measurement module 510 receives from a tandem mass spectrometer at least one measured product ion spectrum from a precursor mass-to-charge ratio range produced by analyzing a sample. Identification module 520 selects a subset of measured product ions from the at least one measured product ion spectrum. Identification module 520 creates a list of candidate compounds that includes a score for each of the candidate compounds. Identification module 520 creates the list by searching a dictionary of potential compounds that includes one or more predicted product ions for each of the potential compounds using the subset of measured product ions. Identification module 520 selects a candidate compound from the list as the identified compound.

Computer Program Product for Search Based on a Product Ion Assumed to Correspond to a Shortened Form of a Peptide In another embodiment of system 500 shown in FIG. 5, measurement module 510 receives from a tandem mass spectrometer at least one measured product ion spectrum from a precursor mass-to-charge ratio range produced by analyzing a sample. Identification module 520 selects a subset of measured product ions from the at least one measured product ion spectrum by selecting a number of measured mono-isotopic product ions from the at least one measured product ion spectrum with the highest intensity and with a mass-to-charge ratio greater than the precursor mass-to-charge ratio range. Identification module 520 searches a protein database in a non-tryptic or semi-tryptic mode specifying the subset of measured product ions as the precursor ions for the search. Identification module 520 selects a full length tryptic peptide from the search results that has a mass to charge ratio in the precursor mass-to-charge ratio range and a non-tryptic or semi-tryptic form with a mass-to-charge ratio matching one of the subset of measured product ions as the identified peptide.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying a compound from tandem mass spectrometry product ions without using any a priori precursor ion information, comprising:
   a tandem mass spectrometer that analyzes a sample producing at least one measured product ion spectrum from a precursor mass-to-charge ratio range; and
   a processor in communication with the tandem mass spectrometer that
   (a) receives the at least one measured product ion spectrum from the tandem mass spectrometer,
   (b) selects a measured product ion from the at least one measured product ion spectrum,
   (c) creates a list of candidate compounds by searching a dictionary of potential compounds with a mass of the selected measured product ion, wherein the dictionary includes one or more predicted product ions for each of the potential compounds and wherein the dictionary is searched using a key that is a product ion mass to retrieve the list of candidate compounds that could produce the product ion mass, and
   (d) for each compound of the list of candidate compounds, comparing one or more predicted product ions found from the dictionary to the at least one measured product ion spectrum to identify at least one compound of the list of candidate compounds with a highest number of predicted product ions matching the at least one measured product ion spectrum.

2. The system of claim 1, wherein the at least one measured product ion spectrum comprises peptide fragments, the dictionary of potential compounds comprises predicted peptides for proteins, the one or more predicted product ions for each of the potential compounds comprise one or more fragments of peptides, the list of candidate compounds comprises candidate peptides, and the identified at least one compound comprises an identified peptide.

3. The system of claim 1, wherein the potential compounds comprise one or more of sugars, lipids, DNA, and RNA.

4. The system of claim 1, wherein the processor selects measured product ions from the at least one measured product ion spectrum by selecting measured mono-isotopic product ions with the highest intensity from the at least one measured product ion spectrum.

5. The system of claim 1, wherein the tandem mass spectrometer analyzes a sample by
dividing a mass range into two or more precursor mass windows, and
fragmenting each precursor mass window of the two or more mass windows, producing a measured product ion spectrum for each precursor mass window.

6. The system of claim 1, wherein the processor further compares the identified at least one compound to the range and
if the identified at least one compound mass-to-charge ratio (m/z) is not found in the precursor mass-to-charge ratio range, determines that the identified at least one compound is a modified form.

7. The system of claim 6, wherein the processor further analyzes a list of modifications to determine a modification that puts the m/z of the modified identified at least one compound in the range.

8. The system of claim 1, wherein the processor further subtracts measured product ions of the identified at least one compound from the at least one measured product ion spectrum and executes steps (b)-(d) again to identify another compound in the sample.

9. A method for identifying a compound from tandem mass spectrometry product ions without using any a priori precursor ion information, comprising:
(a) analyzing a sample using a tandem mass spectrometer, producing at least one measured product ion spectrum from a precursor mass-to-charge ratio range;
(b) receiving the at least one measured product ion spectrum from the tandem mass spectrometer using a processor;
(c) selecting a measured product ion from the at least one measured product ion spectrum using the processor;
(d) creating a list of candidate compounds by searching a dictionary of potential compounds with a mass of the selected measured product ion, wherein the dictionary includes one or more predicted product ions for each of the potential compounds and wherein the dictionary is searched using a key that is a product ion mass to retrieve the list of candidate compounds that could produce the product ion mass using the processor; and
(e) for each compound of the list of candidate compounds, comparing one or more predicted product ions found from the dictionary to the at least one measured product ion spectrum to identify at least one compound of the list of candidate compounds with a highest number of predicted product ions matching the at least one measured product ion spectrum.

10. The method of claim 9, wherein selecting measured product ions comprises selecting a number of measured mono-isotopic product ions with the highest intensity from the at least one measured product ion spectrum.

11. The method of claim 9, wherein the at least one measured product ion spectrum comprises peptide fragments, the dictionary of potential compounds comprises predicted peptides for proteins, the one or more predicted product ions for each of the potential compounds comprise one or more fragments of peptides, the list of candidate compounds comprises candidate peptides, and the identified at least one compound comprises an identified peptide.

12. The method of claim 9, wherein the potential compounds comprise one or more of sugars, lipids, DNA, and RNA.

13. The method of claim 9, wherein selecting the measured product ion comprises selecting measured mono-isotopic product ions with the highest intensity from the at least one measured product ion spectrum.

14. The method of claim 9, wherein analyzing the sample comprises
dividing a mass range into two or more precursor mass windows, and
fragmenting each precursor mass window of the two or more mass windows, producing a measured product ion spectrum for each precursor mass window.

15. The method of claim 9, further comprising
comparing the identified at least one compound to the range and
if the identified at least one compound mass-to-charge ratio (m/z) is not found in the precursor mass-to-charge ratio range, determining that the identified at least one compound is a modified form.

16. The method of claim 15, further comprising
analyzing a list of modifications to determine a modification that puts the mass-to-charge ratio of the modified identified at least one compound in the range.

17. The method of claim 9, further comprising
subtracting measured product ions of the identified at least one compound from the at least one measured product ion spectrum and executing steps (c)-(e) again to identify another compound in the sample.

18. A computer program product, comprising a non-transitory and tangible computer-readable storage medium whose contents include a program with instructions being executed on a processor so as to perform a method for identifying a precursor ion from tandem mass spectrometry product ions without using any a priori precursor ion information, the method comprising:
(a) providing a system, wherein the system comprises one or more distinct software modules, and wherein the distinct software modules comprise a measurement module and an identification module;
(b) receiving from a tandem mass spectrometer at least one measured product ion spectrum from a precursor mass-to-charge ratio range produced by analyzing a sample using the measurement module;
(c) selecting a measured product ion from the at least one measured product ion spectrum using the identification module;
(d) creating a list of candidate compounds by searching a dictionary of potential compounds with a mass of the selected measured product ion, wherein the dictionary includes one or more predicted product ions for each of the potential compounds and wherein the dictionary is searched using a key that is a product ion mass to retrieve the list of candidate compounds that could produce the product ion mass using the identification module; and
(e) for each compound of the list of candidate compounds, comparing one or more predicted product ions found from the dictionary to the at least one measured product ion spectrum to identify at least one compound of the list of candidate compounds with a highest number of predicted product ions matching the at least one measured product ion spectrum using the identification module.

19. The computer program product claim 18, wherein selecting measured product ions comprises selecting a number of measured mono-isotopic product ions with the highest intensity from the at least one measured product ion spectrum.

20. The computer program product of claim 18, wherein the at least one measured product ion spectrum comprises peptide fragments, the dictionary of potential compounds comprises predicted peptides for proteins, the one or more predicted product ions for each of the potential compounds comprise one or more fragments of peptides, the list of candidate compounds comprises candidate peptides, and the identified at least one compound comprises an identified peptide.

* * * * *